(12) United States Patent
Plato et al.

(10) Patent No.: US 8,943,743 B2
(45) Date of Patent: Feb. 3, 2015

(54) **DEVICE FOR ATTRACTING AND CONTROLLING THE COFFEE BERRY BORER, *HYPOTHENEMUS HAMPEI* (COLEOPTERA: SCOLYTIDAE)**

(75) Inventors: Thomas Alfred Plato, Houston, TX (US); Timothy Bruce Johnson, Danville, PA (US); James Scott Plato, League City, TX (US); Stacy Elizabeth Plato, Houston, TX (US)

(73) Assignee: Plato Industries Ltd, Houston, TX (US)

( * ) Notice: Subject to any disclaimer, the term of this patent is extended or adjusted under 35 U.S.C. 154(b) by 1448 days.

(21) Appl. No.: 12/185,196

(22) Filed: Aug. 4, 2008

(65) Prior Publication Data

US 2010/0024279 A1 Feb. 4, 2010

(51) Int. Cl.
*A01M 1/20* (2006.01)
*A01M 1/02* (2006.01)
*A01M 1/04* (2006.01)
*A01M 1/14* (2006.01)
*A01N 25/00* (2006.01)

(52) U.S. Cl.
CPC . *A01M 1/02* (2013.01); *A01M 1/04* (2013.01); *A01M 1/145* (2013.01); *A01M 1/2016* (2013.01); *A01N 25/006* (2013.01)
USPC ............... 43/131; 43/132.1; 43/107

(58) Field of Classification Search
USPC ............ 43/131, 132.1, 107, 122, 114, 121
See application file for complete search history.

(56) References Cited

U.S. PATENT DOCUMENTS

| | | | | |
|---|---|---|---|---|
| 1,427,723 A | * | 8/1922 | Clausen | 43/131 |
| 1,477,273 A | * | 12/1923 | Liss | 43/131 |
| 1,577,351 A | * | 3/1926 | Alvarez | 43/131 |
| 1,787,421 A | * | 12/1930 | Ruddell | 43/107 |
| 3,685,199 A | * | 8/1972 | Bradshaw | 43/114 |
| 3,729,858 A | * | 5/1973 | Bradshaw | 43/114 |
| 3,755,958 A | * | 9/1973 | Bradshaw | 43/114 |
| 3,826,036 A | * | 7/1974 | Neugebauer | 43/131 |
| 3,855,727 A | * | 12/1974 | Canoy | 43/122 |
| 3,972,993 A | * | 8/1976 | Kobayashi et al. | 43/131 |

(Continued)

FOREIGN PATENT DOCUMENTS

| | | | | |
|---|---|---|---|---|
| DE | 19531981 A1 | * | 3/1997 | A01M 1/02 |
| JP | 04179425 A | * | 6/1992 | A01M 1/02 |

(Continued)

OTHER PUBLICATIONS

Paint, Wikipedia, the free encyclopedia, [retrieved on Jun. 14, 2011], 18 pages. Retrieved from the Internet<URL: http://en.wikipedia.org/wiki/Paint>.*

(Continued)

*Primary Examiner* — Darren W Ark
(74) *Attorney, Agent, or Firm* — Defillo & Associates, Inc.; Evelyn A. Defillo

(57) ABSTRACT

The present invention relates to a device coated with a friable composition comprising an insect toxicant wherein the geometry of the device, the presence of openings in the device, the presence of a highly volatile attractant independently located inside the device, and the composition comprising an insect toxicant function together to release an effective concentration of the highly volatile attractant vapor into the environment at a rate that maintains attractancy and at the same time kills the insect as soon as the insect comes into contact with the vapors of the insecticide or the composition impregnated on the surface of the device.

12 Claims, 3 Drawing Sheets

(56) References Cited

U.S. PATENT DOCUMENTS

| | | | |
|---|---|---|---|
| 4,017,030 A * | 4/1977 | Coplan et al. | 43/129 |
| 4,160,335 A * | 7/1979 | Von Kohorn et al. | 43/131 |
| 4,360,987 A * | 11/1982 | Lowder | 43/122 |
| 4,471,563 A * | 9/1984 | Lindgren | 43/122 |
| 4,490,938 A * | 1/1985 | Baker | 43/114 |
| 4,505,065 A * | 3/1985 | Niemeyer | 43/107 |
| 4,638,592 A * | 1/1987 | Schneidmiller | 43/122 |
| 4,671,010 A * | 6/1987 | Conlee et al. | 43/131 |
| 4,694,604 A * | 9/1987 | Mitchell | 43/107 |
| 4,802,303 A * | 2/1989 | Floyd, III | 43/131 |
| 4,930,251 A * | 6/1990 | Crisanti | 43/107 |
| 5,053,223 A * | 10/1991 | Krieg et al. | 424/84 |
| 5,150,541 A * | 9/1992 | Foster et al. | 43/122 |
| 5,290,556 A * | 3/1994 | McKibben et al. | 424/405 |
| 5,311,697 A * | 5/1994 | Cavanaugh et al. | 43/132.1 |
| 5,359,808 A * | 11/1994 | Fitsakis | 43/131 |
| 5,392,558 A * | 2/1995 | Blomquist | 43/107 |
| 5,464,626 A * | 11/1995 | Warren et al. | 43/132.1 |
| 5,540,011 A * | 7/1996 | Groom et al. | 43/107 |
| 5,775,026 A * | 7/1998 | Pearce et al. | 43/132.1 |
| 5,839,221 A * | 11/1998 | Ron et al. | 43/132.1 |
| 5,907,923 A * | 6/1999 | Heath et al. | 43/122 |
| 5,939,062 A * | 8/1999 | Heath et al. | 424/84 |
| 6,112,454 A * | 9/2000 | Plato et al. | 43/122 |
| 6,306,416 B1 * | 10/2001 | McKibben et al. | 424/410 |
| 6,316,017 B1 * | 11/2001 | McKibben et al. | 424/410 |
| 6,339,897 B1 * | 1/2002 | Hayes et al. | 43/132.1 |
| 6,393,760 B1 * | 5/2002 | Lingren | 43/122 |
| 6,430,868 B1 * | 8/2002 | Plato et al. | 43/122 |
| 6,516,558 B1 * | 2/2003 | Lingren et al. | 43/114 |
| 6,625,922 B1 * | 9/2003 | Ernsberger, IV | 43/122 |
| 6,701,663 B1 * | 3/2004 | Hughes et al. | 43/132.1 |
| 6,708,445 B1 * | 3/2004 | Israely | 43/132.1 |
| 6,772,556 B1 * | 8/2004 | Liu | 43/122 |
| 6,811,772 B2 * | 11/2004 | Thoenes | 43/131 |
| 6,966,142 B1 * | 11/2005 | Hogsette et al. | 43/132.1 |
| 7,093,389 B1 * | 8/2006 | Meier et al. | 43/132.1 |
| 7,290,368 B2 * | 11/2007 | Rich et al. | 43/122 |
| 7,310,907 B2 * | 12/2007 | Suteerawanit | 43/122 |
| 7,402,302 B2 * | 7/2008 | Plato et al. | 43/132.1 |
| 7,412,797 B1 * | 8/2008 | Hiscox | 43/122 |
| 7,458,183 B2 * | 12/2008 | Meier et al. | 43/132.1 |
| 7,694,456 B1 * | 4/2010 | Curtis | 43/107 |
| 7,712,248 B2 * | 5/2010 | Beroza | 43/132.1 |
| 7,856,753 B2 * | 12/2010 | Fisher | 43/132.1 |
| 8,418,399 B2 * | 4/2013 | Palencia-Adrubau et al. | 43/107 |
| 2002/0144452 A1 * | 10/2002 | Beroza | 43/107 |
| 2003/0049296 A1 * | 3/2003 | Knauf et al. | 43/107 |
| 2004/0055207 A1 * | 3/2004 | Beroza | 43/131 |
| 2004/0231231 A1 * | 11/2004 | Cataldo et al. | 43/132.1 |
| 2004/0234567 A1 * | 11/2004 | Dawson | 424/405 |
| 2005/0144831 A1 * | 7/2005 | Knauf et al. | 43/107 |
| 2006/0057177 A1 * | 3/2006 | Hojo et al. | 424/405 |
| 2006/0086039 A1 * | 4/2006 | Israely et al. | 43/131 |
| 2006/0123694 A1 * | 6/2006 | Welch | 43/107 |
| 2006/0207163 A1 * | 9/2006 | Frokopy | 43/131 |
| 2006/0248783 A1 * | 11/2006 | Lindquist et al. | 43/114 |
| 2006/0260183 A1 * | 11/2006 | Hockaday | 43/132.1 |
| 2006/0265942 A1 * | 11/2006 | Watson | 43/114 |
| 2006/0283076 A1 * | 12/2006 | Chambers et al. | 43/114 |
| 2007/0094915 A1 * | 5/2007 | Plato et al. | 43/107 |
| 2007/0157506 A1 * | 7/2007 | Sadovski et al. | 43/114 |
| 2007/0289202 A1 * | 12/2007 | Spencer | 43/131 |
| 2008/0044446 A1 * | 2/2008 | McKibben | 43/107 |
| 2008/0086932 A1 * | 4/2008 | Cook et al. | 43/107 |
| 2008/0184614 A1 * | 8/2008 | Higbee et al. | 43/132.1 |
| 2008/0236027 A1 * | 10/2008 | Plato et al. | 43/129 |
| 2008/0256843 A1 * | 10/2008 | Hack et al. | 43/131 |
| 2009/0000180 A1 * | 1/2009 | Palencia-Adrubau et al. | 43/131 |
| 2009/0071060 A1 * | 3/2009 | McKay | 43/122 |
| 2009/0084024 A1 * | 4/2009 | Hamilton Baxter | 43/131 |
| 2009/0183419 A1 * | 7/2009 | Harris | 43/132.1 |
| 2009/0293342 A1 * | 12/2009 | Winkler | 43/114 |
| 2010/0154289 A1 * | 6/2010 | Fisher | 43/107 |
| 2010/0154290 A1 * | 6/2010 | Fisher | 43/107 |
| 2010/0242339 A1 * | 9/2010 | Cuellar Bernal | 43/107 |
| 2010/0275505 A1 * | 11/2010 | Kagawa | 43/107 |
| 2010/0325941 A1 * | 12/2010 | Bolin | 43/131 |
| 2013/0298446 A1 * | 11/2013 | Rubel | 43/132.1 |
| 2013/0302269 A1 * | 11/2013 | Gomez et al. | 43/107 |

FOREIGN PATENT DOCUMENTS

| | | | | |
|---|---|---|---|---|
| JP | 05015285 A * | 1/1993 | | A01M 1/02 |
| JP | 05015286 A * | 1/1993 | | A01M 1/02 |
| JP | 05076264 A * | 3/1993 | | A01M 1/02 |
| WO | WO 0164032 A1 * | 9/2001 | | A01M 1/02 |

OTHER PUBLICATIONS

Paint glossary, R&D Money Company,[retrieved on Jun. 14, 2011], 5 pages. Retrieved from the Internet<URL: http://www.rdmoney.com/paint_glossary.htm>.*

Edward Winston et al; Arabica Coffee Manual for Lao PDR; Chapter 9, 2005; AE939/E.

Silvestre, Fernández y Cordero, Julio. Evaluación de atrayentes alcohólicos en trampas artesanales para el monitoreo y control de la broca del café, *Hypothenemus hampei* (Ferrari). *Bioagro*. Sep. 2005, vol. 17, No. 3, p. 143-148. ISSN 1316-3361.

* cited by examiner

DEVICE FOR ATTRACTING AND CONTROLLING THE COFFEE BERRY BORER, *HYPOTHENEMUS HAMPEI* (COLEOPTERA: SCOLYTIDAE)

FIELD OF THE INVENTION

The present invention relates to a method and a device for controlling coffee plant pests, such as the coffee berry borer, *Hypothenemus hampei* Ferrari (Coleoptera: Scolytidae) and the coffee leaf miner, (*Perileucoptera coffeella* Guérin-Méneville (Lepidoptera: Lyonetiidae).

BACKGROUND OF THE INVENTION

The coffee berry borer (hereafter called CBB) is a small beetle native to Africa that has spread throughout much of the coffee producing areas of the world. It is recognized as the most harmful pest to coffee crops worldwide.

The small female CBB lays multiple eggs inside the coffee berry, which hatch into larvae that feed upon the coffee seeds (seeds that later will develop into the beans) inside the berry. After pupating, the adult CBB emerge inside the berry where mating occurs. Only the female CBB has functional wings; thus it is the mated female that emerges from the berry to search for new coffee berries as oviposition sites to perpetuate the species.

The presence of this pest negatively affects the economy of over 20 million families that depend on coffee production in over seventy countries, including coffee producing countries in Latin America and the Caribbean, causing significant damage as high as 50% yield losses. Infested coffee beans reduce the price to growers, as well as reduce the size of the crop yield at harvest. In severe infestations the CBB can economically damage the entire harvest of an area.

There are a few natural enemies of the CBB, such as the parasitic wasp (*Phymastichus coffea*). Unfortunately, the effectiveness of the wasp in controlling the CBB is not yet fully known.

As this point, the main measures for controlling the CBB are only preventative applications of persistent insecticides. The implementation of efficient control programs is difficult, since the coffee plant is perennial, with several flowering periods, and generally grows in areas of hilly terrain with very unpredictable weather. Furthermore, the chemical control of this pest is difficult as the borer spends most of its life cycle deep inside the coffee berry.

The prior art shows the use of endosulfan 35 EC, an old organo-chlorine based chemical insecticide, to control the female beetles after they emerge from the coffee berries 1) that are not harvested or 2) that do not abscise from the tree or 3) those that fall to the ground at the base of the tree but before they oviposit in new berries. In addition, Cypermethrin and Deltamethrin, pyrethoids at 26 ml/15 L of water are also used by the prior art to control CBB.

Unfortunately, emerging resistance of the CBB to these products is beginning to reduce the chemicals' effectiveness over the pest. In addition, there have been many cases of accidental human poisoning. Furthermore, the use of the endosulfan insecticide raises additional concern regarding environmental contamination and residues of the chemical from repeated applications.

The prior art uses commercial traps+alcohol based attractants, such as the BROCAP™ (FIG. 3), the Fiesta Trap (FIG. 4), or homemade versions made from plastic 1.5 liter soda bottles, in mass trapping programs as alternatives to control CBB populations. Unfortunately, these traps are expensive, difficult to maintain, and/or service. Basically, it is necessary to service the traps on a weekly basis to remove captured insects and to refresh the soapy water that captures the insects.

The second major pest in the coffee plantations of Central and South America is the coffee-leaf miner, *Perileucoptera coffeella* Guérin-Méneville (Lepidoptera: Lyonetiidae). This pest is endemic in the West Indies and in Madagascar.

This pest is economically significant to the coffee producers because the larvae spend their lives burrowing in the palisade layer of coffee leaves, which can lead to considerable destruction of assimilatory surface areas. The resulting leaf fall causes large reductions in field yields, particularly if it occurs a few weeks before the berries are harvested. The leaf damage can also result in the weakening of fruiting branches or even of the whole tree, and recovery does not take place until the following season.

Leaf miners are difficult to control because they live burrowed into the leaves in round individual tunnels. Pupation takes place in cocoons on the undersides of the leaves. Because of their life habits, chemical control of leaf-miners requires repeated applications of insecticides with systemic activity. The sex pheromone of the coffee leaf miner is described in U.S. Pat. No. 5,053,223 as a mixture of 5,9-dimethylpentadecane and 5,9-dimethylhexadecane.

In view of the above, there is a need for a method and apparatus that kills pests affecting the coffee plants but do not suffer the disadvantages of the prior art of insecticides and traps described above; a system that can lower the chemical residues on the plant, and is economical and environmentally friendly.

SUMMARY OF THE INVENTION

It is an objective of the present invention to provide a coffee plant pest control device that is highly effective, and yet, inexpensive, easy to use, maintenance free, and environmentally safe.

One aspect of the present invention is described as a composition that is used to coat a perforated cylinder and used in combination with a dispenser loaded with a chemical attractant inside the cylinder.

The composition comprises:
a binder,
a pigment,
an insect toxicant, and
an ingredient that is both a filler and a thickener.

There is also the option of including a feeding stimulant in the composition.

The present invention also contemplates a device for combating insects by attracting the insects and then destroying them following their arrival on said device.

The device comprises:
an elongated body, the elongated body having a top end, a bottom end, and a plurality of openings;
wherein the bottom end includes an aperture;
an independent dispenser placed inside the elongated body,
wherein the dispenser is introduced inside the elongated body by the bottom aperture;
wherein the dispenser includes a composition comprising at least one volatile liquid attractant for attracting the insect;
wherein the dispenser includes an output from which the vapors of the attractant diffuse until reaching the plurality of openings and dispersing into the surrounding atmosphere;
wherein said output is adjustable in order to achieve maximum attraction of said insect and uniform emission of said at least one attractant; and wherein the elongated body is coated with a composition comprising: a binder, an insect attracting pigment, an insect toxicant, an insect feeding stimulant, and an ingredient which is both a filler and a thickener.

Furthermore, the present invention contemplates a method for combating insects by attracting the insects to a device and then destroying them following their arrival on said device. The method comprising the steps of:

a) hanging at least one of the devices of claim 1 in a location suspected of being infested by at least one of a targeted insect;
b) placing the dispenser containing the attractant into the device;
c) releasing the attractant from the dispenser to the openings of the device;

wherein the insect is destroyed upon contact with the device.

The present invention is deployed at a rate of 12 to 28 per hectare throughout the coffee orchard, instead of along the field perimeter, and is installed on the coffee tree branches (not on wooden stakes).

DETAILED DESCRIPTION OF THE INVENTION

The present invention relates to a device coated with a friable composition comprising an insect toxicant wherein the geometry of the device, the presence of openings in the device, the presence of a highly volatile attractant independently located inside the device, and the composition comprising an insect toxicant function together to release an effective concentration of the highly volatile attractant vapor into the environment at a rate that maintains attractancy and at the same time kills the insect as soon as the insect comes into contact with the vapors of the insecticide or the composition impregnated on the surface of the device.

In the present invention, the insects are attracted by a variety of stimuli:

By means of an odoriferous substance (attractant);

By means of a suitable color of the device that is particularly attractive to the insect;

By means of the device itself, whose shape resembles a fruit or host plant (optical/visual attraction).

The present inventors have found that the distance between the surface of the volatile liquid attractant held within the device and the aperture through which the attractant is released and the diameter of the aperture affects the release rate of the vapor. In view of this, the present inventors have designed a device to insure that the vapor space remains saturated by attractant vapor and minimizes the change in height of the vapor space over time to dispense the attractant.

In one embodiment of the present invention a homogeneous friable composition is described that is used to coat the device used in combination with a dispenser loaded with a highly volatile attractant, which is located inside the device.

Composition

The composition according to the present invention comprises:

a binder, a pigment, a toxicant regeneration enhancer;

an insect toxicant, and an ingredient that is both a filler and a thickener.

There is also the option of including a feeding stimulant in the composition.

In one embodiment, the composition may include a polymer, at least one insect pheromone, at least one insect feeding stimulant, and an insect toxicant.

Binder

The composition of the present invention includes a binder, such as various synthetic and natural resins typically used in paints and coatings, though modified to cause the coated surface to be friable enough to allow insects to bite off and ingest the material, while still maintaining the structural integrity of the coating.

Examples of binders useable in the present invention include one or more of shellac, shellac with waxes, natural waxes, chemically modified waxes and synthetic waxes, acrylics, epoxies, alkyds, polyurethanes, linseed oil, tung oil, methyl cellosolve, polyvinylpyrrolidone, polyvinyl alcohol, polyacrylates, polymethacrylates, sugars, starch, alginates, agar, lignosulphonates and gum Arabic.

Pigment

The composition of the present invention also includes a pigment. The color of the pigment is selected according to which color(s) will attract the targeted insect(s).

Other pigments which may be used in the present invention are described in the Modern Plastics Encyclopedia published by McGraw Hill, New York, N.Y.

Insect Toxicant

The composition of the present invention comprises at least one insect toxicant. The insect toxicant(s) is/are selected based upon the type of insect(s) to be controlled or eradicated.

Some examples of insect toxicants useable in the present invention are: organophosphates such as malathion, pyrethroids, carbamates, spinosyns, pyridines, pyrroles or pyrazoles, thiadiazines, oxadiazines, neem oil, nicotinoids, anthranilic diamides and others.

Attractant

Attractant refers to any liquid chemical composition that includes an individual compound or a composition including more than one compound that either directly or indirectly, such as into the wind, causes the insect to gravitate toward the attractant. Examples of useful attractants in the present invention include, for example, various ratios of ethyl and methyl alcohol for coffee berry borer and a mixture of 5,9-dimethylpentadecane and 5,9-dimethylhexadecane for coffee leaf miner.

A variety of volatile liquid compositions can be found having a vapor pressure within this useful range. One volatile attractant we have found that is useful in the controlled release system of the invention comprises absolute ethanol or denatured absolute ethanol. Such material can be dispensed by the controlled release device of the invention at a rate of about 0.02 to about 0.2 grams per hour for the purpose of attracting typically flying insect pests.

The ratio of the alcohols used in the field tests is 3:1 methyl to ethyl alcohol.

In the present invention in order to attract the female coffee berry borer to the device, a small slow release dispenser, filled with a kairomone that comprises a 75/25 mixture of methyl alcohol and ethyl alcohol, is placed vertically in the bottom of the device. The ratio of ethyl and methyl alcohol can vary with the preferred mixture consisting of 3 parts methyl alcohol and 1 part ethyl alcohol.

As the alcohol mixture evaporates, the chemical is released through the orifice of the bottle containing the kairomone and through the openings of the device creating a chemical plume that attracts the CBB to land on the tube. Within seconds after contacting the insecticide vapors of or landing on the tube, the coffee berry borer receives a toxic dose of insecticide and becomes incapacitated.

It is required that the attractant(s) used in the present invention be released as a vapor at a controlled rate for the purpose of attracting the insect pests.

In the preferred embodiment of the invention, 15 ml of 3 parts methyl alcohol and 1 part ethyl alcohol are added to a bottle measuring 7 cm in length with an orifice 0.4 mm in diameter. The alcohol mixture can be mixed prior to adding to the bottle or the two components can be added separately.

The Device

The device according to the present invention is designed in such a way that the coffee pest insect perceives it as a harmless solid body when viewed from a distance. The insect gets closer to the device by the effect of the color of the device and the highly volatile attractant. As the pest touches the device or inhales the vapors of the toxicant, the toxicant kills the pest.

Figure 5:
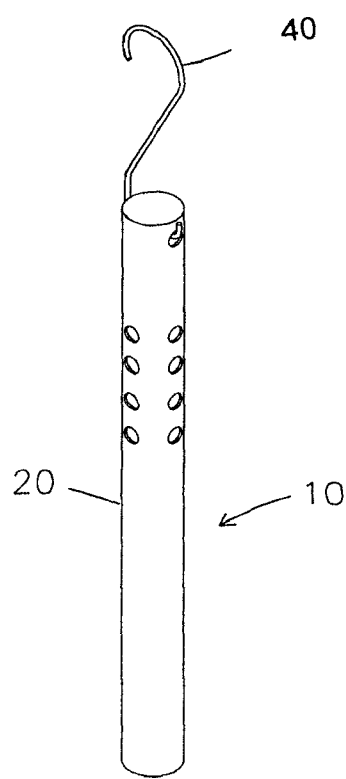
FIG. 5 illustrates the device of the present invention coated with the composition of the present invention having an ethyl/methyl alcohol dispenser inside the device of the present invention.
Figure 6:
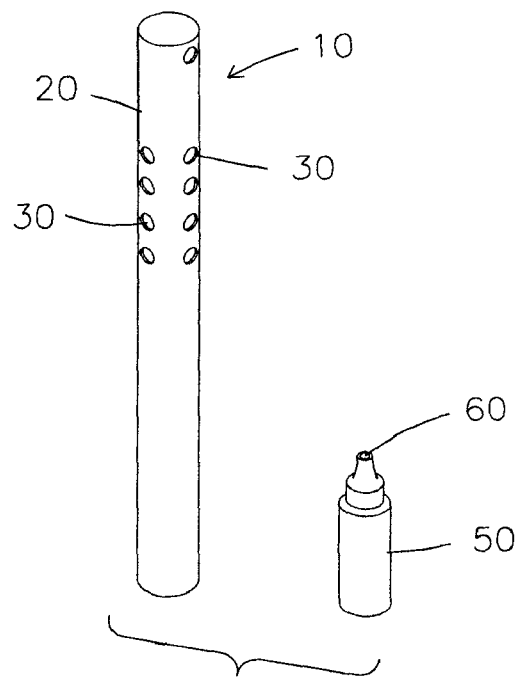
FIG. 6 illustrates the device of the present invention including the dispenser.

FIG. 5 shows the device according to the present invention. The device 10 uses a 12 inch tube 20 that functions as the "kill station". The tube is perforated with a plurality of openings 30 and coated with the homogeneous composition according to the present invention.

In one embodiment of the present invention, the device is fitted at its top with a means for hanging 40.

The present invention is designed to allow prolonged, uniform emission into the atmosphere of the attractant over long periods of time by allowing the active ingredient to pass through narrow openings of the device 10.

The device 10 is placed in the coffee plants usually by hanging the device in the plants. The devices are checked periodically, typically every 2 weeks to ensure that they are complete and properly hung on the tree. With the present invention, there is no need to replenish the attractant for at least several weeks, up to 90-120 days. Thus, when an infested area is located or detected with damaged berries, 12 to 28 devices are deployed in the area to control, and/or eradicate the targeted pest.

If the target species is the coffee leaf miner, a dispenser containing the female sex pheromone of the coffee leaf miner is placed inside the tube. A variety of materials, known to those skilled in the art, can be used to create a device to release the female sex pheromone over a sustained duration. The sex pheromone of the coffee leaf miner is 5,9-dimethylpentadecane and 5,9-dimethylhexadecane and is described in U.S. Pat. No. 5,053,223. Male coffee leaf miners are attracted by the chemical plume and receive a toxic dose of insecticide after landing on the tube and become incapacitated. If a sufficient number of male coffee leaf miners are killed, successful mating with female moths is prevented, thereby reducing the subsequent generation of leaf miner larvae.

The device includes a bottom opening (not shown) that is used to insert the dispenser container 50 having the attractant inside the device 10.

In a less preferable embodiment, the device 10 may be spherical, cylindrical, in the form of a cube, a rectangular prism, an oval prism, or pyramidal. The preferred shape for the device of the present invention is an elongated cylindrical tube.

The overall dimensions of the device of the present invention are important in order to prevent a large change in the distance between the surface of the volatile attractant/vapor interface and the orifices in the device.

The openings in the device can be of any shape. However, the present inventors have found that the circular or oval shape is most easily manufactured. The apertures can be about 0.5 to 1.5 cm in diameter, preferably 0.8 to 1.0 cm.

It was found that the size of the dispenser container's orifice 60 is important in controlling the release rate of the kairomone attractant. Accordingly, the orifice should preferably be in the range of 0.2-1.0 mm.

For a dispenser container holding 15 ml of volatile liquid attractant, the device of the present invention should have 1 inch inside diameter, 0.08 inches of thickness and 12 inches in length.

The device is preferably made of biodegradable fiber board with an outer layer of white litho paper (T&S Products, Arlington, Tex.) and has preferably sixteen ⅜" perforations at the upper level for releasing of the kairomone or pheromone plume, plus two additional perforations at the top for securing a hanger and two perforations at the bottom.

The device can be prepared from any barrier material capable of preventing any significant diffusion or permeation of the attractant through the material. Typical materials for the device of this invention include: thermoplastic materials such as polyethylene, polypropylene, polyvinylchloride, polyester (polyethylene terephthalate, polybutylene terephthalate), etc. The choice of materials is not critical except that the barrier material should be inert to insect attractants, be moldable or shapeable into the device of the invention, and can be easily assembled.

Accordingly, at ambient temperatures, generally about 20 to 35° C., the device should contain at least about 14 to 15 ml of the attractant to release for 90-120 days. Each 45 to 60 days a new TMB will replace the old TMB and the dispenser will be inserted in the new TMB of the remaining 45 to 60 days.

EXAMPLE

Ingredients in the coating mixture:

| | |
|---|---|
| Denatured ethyl alcohol (SDA 23A) | 30.0% |
| Solvents and Chemicals, Pearland, TX | 19.8% |
| Wax containing shellac (Tigerlac #5052) | |
| Kane International | |
| Rye, New York | |

The denatured ethyl alcohol is a solvent for the wax, and combined, the two ingredients make up the binder in the mixture. Most of the alcohol evaporates during the manufacturing process.

| | |
|---|---|
| Pigment | 4.7% |
| Carolina Color | |
| Lancaster, TX | |
| Kaolin Clay (Burgess #80) | 10.2% |
| Raw Materials Corp. | |
| Houston, TX | |
| Functions as a filler and a thickener | |
| Cotton Seed Oil (crude) | 18.9% |

| | | |
|---|---|---|
| Archer Daniels Richmond, TX Other sources of vegetable-based oils can be used | | |
| Malathion ULV 95% Cheminova USA Wayne, NY | 10.0% | |

Other insecticides can be used.

After the ingredients of the coating mixture are combined, the perforated tubes are dipped into the mixture two or three times until thoroughly coated.

The kairomone dispenser is a 15 ml nalgene bottle filled with a 75/25 mixture of methyl and ethyl alcohols. The dispenser bottle is inserted into the bottom of the tube prior to hanging in the coffee plantation.

Field Trials

Figure 1:
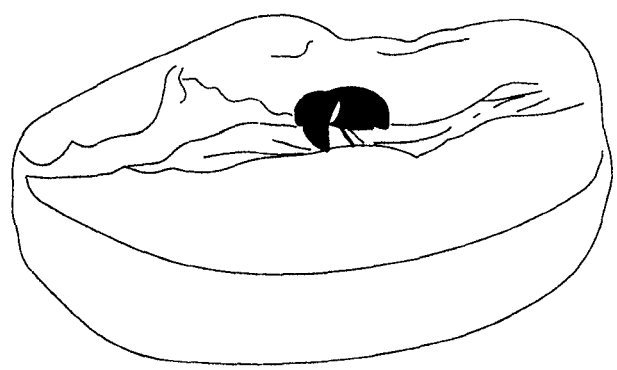
FIG. 1 illustrates an electron micrograph of a female coffee berry borer.
Figure 2:
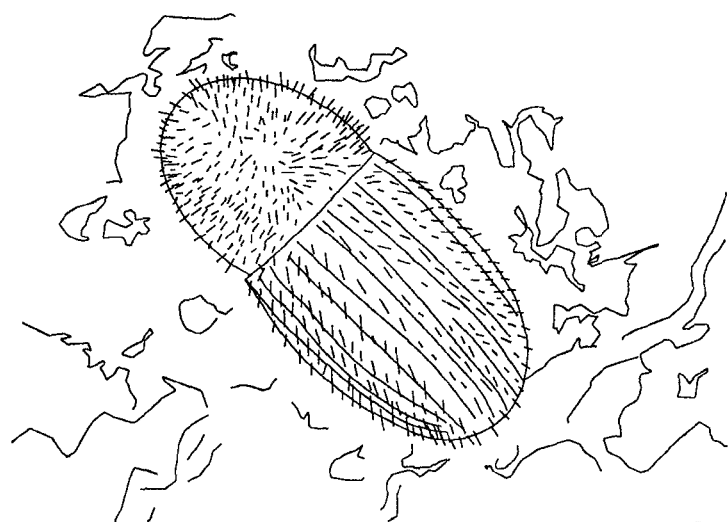
FIG. 2 illustrates a photograph of an adult coffee berry borer on a coffee bean.
Figure 3:
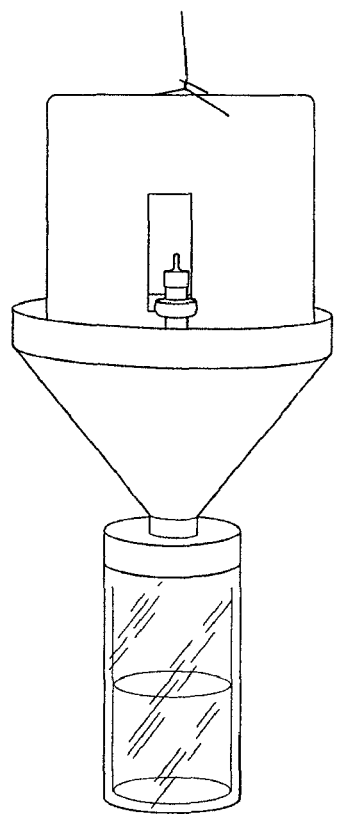
FIG. 3 illustrates the BROCAP Trap device according to the prior art.
Figure 4:
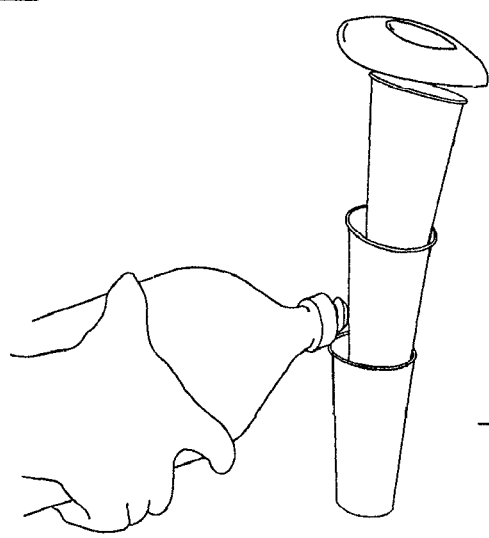
FIG. 4 illustrates the FIESTA Trap device according to the prior art.

A study was established in a coffee plantation in Costa Rica in 2007 to compare the efficacy of the device of the present invention Tubos Mata Brocas (hereafter called TMB) to a mass trapping program using the Fiesta Trap of the prior art (FIG. 4) for control of CBB during an 80-day period following peak bloom.

The test included three blocks of coffee production. Each block was about 3 hectares or 7.5 acres in size. The block treated with TMBs was further subdivided into 30 equally sized areas where 10 sub-plots were each treated with the Tubos Mata Brocas, manufactured with either red, yellow, or white pigments as part of the coating composition. A total of 60 TMB tubes were deployed throughout the 3 hectare block. Malathion was included in the TMB composition as the toxicant. A second block was treated with Fiesta Traps under a mass trapping protocol while a third block was left untreated for comparison purposes. At the end of the 80 day period, each block was sampled for damaged coffee berries.

| Treatment | Mean % infested berries1 | Transformed data[2] ✓ |
|---|---|---|
| 1) Block treated with TMBs | 2.70 a | 1.49 a |
| 2) Block treated with Fiesta Traps | 6.10 a | 2.37 b |
| 3) Untreated blocks | 15.00 b | 3.61 c |
| C.V. | 88% | 40% |

[1] Numbers sharing a common letter are not statistically different (Turkey's $P = 0.05$).
[2] Data transformed with square root.

The block treated with the TMBs had 56% fewer damaged berries than did the block treated with Fiesta Traps under a mass trapping protocol. Both the TMB and Fiesta Trap blocks had significantly fewer infested berries than did the block that received no treatment. When the data were transformed to reduce variability, the TMB block had significantly fewer damaged berries compared to the block treated with the Fiesta Traps ($P=0.05$).

A second study was conducted in 2008 near Naranjo, Costa Rica. In this study, blocks treated with either blue and red TMBs had fewer damaged berries 70 days after treatments were initiated than did the untreated block or the block treated with endosulfan. Each block was 2500 m$^2$ in size and was treated with 20 TMBs per hectare.

| Treatment | Mean % infested berries1 |
|---|---|
| 1) Block treated with red TMBs | 0.70 |
| 2) Block treated with blue TMBs | 0.25 |
| 3) Block treated with endosulfan | 1.15 |
| 4) Untreated block | 1.15 |

A third study was conducted in 2008 near Alajuela, Costa Rica. In this study, 2500 m$^2$ blocks treated with either blue and red TMBs at a rate of 20 TMBs per hectare had fewer damaged berries 70 days after treatments were initiated than did the untreated block, the block treated with endosulfan, or the block treated with red plastic traps.

| Treatment | Mean % infested berries1 |
|---|---|
| 1) Block treated with red TMBs | 2.1 |
| 2) Block treated with blue TMBs | 0.6 |
| 3) Block treated with red plastic 18" × 18" sticky squares | 2.8 |
| 3) Block treated with endosulfan | 5.9 |
| 4) Untreated block | 3.85 |

What is claimed is:

1. A device for combating insects by attracting the insects and then destroying them, following their arrival on said device, the device comprising:
    an elongated body, the elongated body having a top end, a bottom end, and a plurality of openings, wherein the openings each have a diameter between 0.2 and 1.0 mm;
    an independent dispenser placed near the bottom end of the elongated body;
    wherein the dispenser includes a liquid and highly volatile insect attractant;
    wherein vapors of the attractant diffuse through an output on the dispenser until reaching the plurality of openings and dispersing into a surrounding atmosphere;
    wherein the elongated body is entirely coated with a composition comprising: a binder, an insect attracting pigment, an insect toxicant, and an insect feeding stimulant; and
    wherein the binder is selected from shellac, shellac with waxes, polymers, natural waxes, chemically modified waxes and synthetic waxes, acrylics, epoxies, alkyds, polyurethanes, linseed oil, tung oil, methyl cellosolve, polyvinylpyrrolidone, polyvinyl alcohol, polyacrylates, polymethacrylates, starch, alginates, agar, lignosulphonates and gum Arabic.

2. The device of claim 1, wherein the composition comprises: from about 17% to about 35% by weight of the binder, from about 1% to about 12% by weight of the insect attracting pigment, from about 1% to about 40% by weight of the insect toxicant, from about 1% to about 23% by weight of the insect feeding stimulant, and from about 1% to about 17% by weight of an ingredient, which is both a filler and a thickener.

3. The device of claim 1, wherein the composition comprises: from about 17% to about 35% by weight of the binder comprising shellac, from about 23% to about 64% by weight of the insect feeding stimulant comprising ethyl alcohol, from about 1% to about 12% by weight of the insect attracting pigment, from about 1% to about 40% by weight of the insect toxicant, and from about 1% to about 23% by weight of a crude cottonseed oil, and from about 1% to about 17% by weight of the ingredient, which is both a filler and a thickener, comprising clay filler.

4. The device of claim 1, wherein the composition comprises from about 17% to about 35% by weight of the binder, from about 1% to about 12% by weight of the insect attracting pigment, from about 1% to about 40% by weight of the insect toxicant, from about 1% to about 23% by weight of the insect feeding stimulant, and from about 1% to about 17% by weight of an ingredient, which is both a filler and a thickener.

5. The device of claim 1, wherein said composition further includes an ingredient, which is both a filler and a thickener, and sufficient solvent to solubilize said ingredient, which is both a filler and a thickener.

6. The device of claim 5, wherein said solvent is selected from the group consisting of ethyl alcohol, methyl alcohol, chlorinated hydrocarbons, petroleum solvents, turpentine, xylene, and mixtures thereof.

7. The device of claim 1, wherein said composition further includes an ingredient, which is both a filler and a thickener, said ingredient, which is both a filler and a thickener, is an organic composition selected from the group consisting of methyl cellulose, ethyl cellulose, and mixtures thereof.

8. The device of claim 1, wherein said insect toxicant is selected from the group consisting of organophosphates comprising malathion, pyrethroids, carbamates, spinosyns, pyridines, pyrroles or pyrazoles, thiadiazines, oxadiazines, neem oil, nicotinoids, fiprole insecticides, anthranilic diamides and mixtures thereof.

9. The device of claim 1, wherein said elongated body has an outer diameter of from about 1/8 inch to about 1 1/2 inches and is from about 6 inches to 2 feet in length.

10. The device of claim 1, wherein said insect attracting pigment comprises a red or blue color.

11. A device for combating insects by attracting the insects and then destroying them, following their arrival on said device, the device consisting of:
an elongated body, the elongated body having a top end, a bottom end, and a plurality of openings, wherein the openings each have a diameter between 0.2 and 1.0 mm;
an independent dispenser placed near the bottom end of the elongated body;
wherein the dispenser includes a liquid and highly volatile insect attractant;
wherein vapors of the attractant diffuse through an output on the dispenser until reaching the plurality of openings and dispersing into a surrounding atmosphere;
wherein the elongated body is entirely coated with a mixture comprising: a binder, an insect attracting pigment, an insect toxicant, an insect feeding stimulant, and an ingredient, which is both a filler and a thickener; and
wherein the binder is selected from shellac, shellac with waxes, polymers, natural waxes, chemically modified waxes and synthetic waxes, acrylics, epoxies, alkyds, polyurethanes, linseed oil, tung oil, methyl cellosolve, polyvinylpyrrolidone, polyvinyl alcohol, polyacrylates, polymethacrylates, starch, alginates, agar, lignosulphonates and gum Arabic.

12. A device for combating insects by attracting the insects and then destroying them, following their arrival on said device, the device comprising:
an elongated body, the elongated body having a top end, a bottom end, and a plurality of openings, wherein the openings each have a diameter between 0.2 and 1.0 mm;
an independent dispenser place near the bottom end of the elongated body;
wherein the dispenser includes a liquid and highly volatile insect attractant including kairomone in a 3:1 mixture of methyl alcohol and ethyl alcohol or 5,9-dimethylpentadecane and 5,9-dimethylhexadecane;
wherein the elongated body is entirely coated with a composition comprising: a binder, an insect attracting pigment, an insect toxicant, an insect feeding stimulant, and an ingredient, which is both a filler and a thickener; and
wherein the binder is selected from shellac, shellac with waxes, polymers, natural waxes, chemically modified waxes and synthetic waxes, acrylics, epoxies, alkyds, polyurethanes, linseed oil, tung oil, methyl cellosolve, polyvinylpyrrolidone, polyvinyl alcohol, polyacrylates, polymethacrylates, starch, alginates, agar, lignosulphonates and gum Arabic.

* * * * *